United States Patent [19]

Bard et al.

[11] Patent Number: 5,221,605
[45] Date of Patent: * Jun. 22, 1993

[54] LUMINESCENT METAL CHELATE LABELS AND MEANS FOR DETECTION

[75] Inventors: Allen J. Bard, Austin, Tex.; George M. Whitesides, Newton, Mass.

[73] Assignee: Igen, Inc., Rockville, Md.

[*] Notice: The portion of the term of this patent subsequent to Apr. 27, 2007 has been disclaimed.

[21] Appl. No.: 609,072

[22] Filed: Oct. 30, 1990

Related U.S. Application Data

[63] Continuation of Ser. No. 666,987, Oct. 31, 1984, abandoned.

[51] Int. Cl.⁵ .................. C07F 15/00; C12Q 1/00; C12Q 1/68; G01N 33/532
[52] U.S. Cl. .................. 435/4; 435/5; 435/6; 435/7.1; 436/550; 436/543; 436/805; 436/806; 530/391.5; 530/402; 544/225; 546/2; 546/10; 546/12; 548/101; 548/109
[58] Field of Search ............ 435/4, 5, 6, 7.1; 436/546, 800, 805, 806, 543, 500; 530/389, 391, 802, 391.5, 402; 546/2, 10, 12; 544/225; 540/145; 536/1.1; 548/101, 109

[56] References Cited

U.S. PATENT DOCUMENTS

| | | | |
|---|---|---|---|
| 3,504,052 | 3/1970 | Neuse et al. | 525/389 |
| 3,530,049 | 9/1970 | Scherzer et al. | 205/247 |
| 3,793,355 | 2/1974 | Wilkinson | 556/21 |
| 3,804,869 | 4/1974 | Chabardes et al. | 546/2 |
| 3,966,556 | 6/1976 | Rubenstein et al. | 435/188 |
| 3,996,345 | 12/1976 | Ullman et al. | 436/537 |
| 4,058,732 | 11/1977 | Wieder | 250/461.1 |
| 4,199,559 | 4/1980 | Ullman et al. | 436/537 |
| 4,205,952 | 6/1980 | Cais | 436/518 |
| 4,220,722 | 9/1980 | Rowley | 435/188 |
| 4,238,195 | 12/1980 | Bogusldski | 422/61 X |
| 4,238,395 | 12/1980 | Buckler et al. | 436/800 |
| 4,277,437 | 7/1981 | Maggio | 422/61 X |
| 4,280,815 | 7/1981 | Oberhardt | 436/518 |
| 4,293,310 | 10/1981 | Weber | 436/536 |
| 4,352,751 | 10/1982 | Wieder et al. | 436/500 |
| 4,363,759 | 12/1982 | Boguslaski et al. | 436/546 |
| 4,374,120 | 2/1983 | Soini et al. | 436/546 |
| 4,432,907 | 2/1984 | Wieder | 534/16 |
| 4,637,988 | 1/1987 | Hinshaw et al. | 436/546 |
| 4,687,747 | 8/1987 | Lin | 436/518 |
| 4,699,978 | 10/1987 | Barton | 536/27 |
| 4,707,454 | 11/1987 | Hendrix | 436/546 |
| 4,745,076 | 5/1988 | Muller et al. | 436/537 |
| 4,772,548 | 9/1988 | Stavrianpoulos | 435/5 |
| 4,943,523 | 7/1990 | Stavrianpoulos | 436/537 |
| 4,946,958 | 8/1990 | Campbell et al. | 530/802 |

FOREIGN PATENT DOCUMENTS

| | | |
|---|---|---|
| 17402 | 7/1983 | Australia . |
| 0178450 | 4/1986 | European Pat. Off. . |
| WO81/01883 | 7/1981 | PCT Int'l Appl. . |

OTHER PUBLICATIONS

White et al., J. Amer. Chem. Soc., 104: 6891-95 (1982).
Rubinstein et al., J. Amer. Chem. Soc. 103: 512-16 (1981).

(List continued on next page.)

*Primary Examiner*—David Saunders
*Attorney, Agent, or Firm*—Barry Evans

[57] ABSTRACT

A chemical moiety is disclosed which comprises a chemical biochemical, or biological substance attached to one or more electrochemiluminescent organometallic compounds. In a preferred embodiment of the invention the substance is attached to one or more ruthenium-containing or osmiumcontaining luminescent organometallic compounds. Methods are disclosed for detecting very small amounts of the chemical moiety using chemiluminescent, electrochemiluminescent, and photoluminescent means. Compounds are disclosed which are useful for labelling substances of interest with ruthenium-containing and osmium-containing labels or other electrochemiluminescent labels. These labelled substances are useful in methods provided for detecting and quantifying analytes of interest in binding assays and competitive binding assays. The labelled substances are of particular use in homogeneous binding assays. These methods form the bases for systems designed to enable the rapid, efficient, and sensitive determination of a broad array of chemical, biochemical, and biological materials of interest.

12 Claims, No Drawings

OTHER PUBLICATIONS

Sprintschnik et al. J. Amer. Chem. Soc. 99(15) pp. 4947–4954 (1977).

Davidson Chemical Abstracts 108: 146746t (1988).

Weber et al. Clinical Chemistry vol. 29, No. 9, 1983, pp. 1665–1672.

Factors Influencing the Luminescent Emission States of the Rare Earths, vol. 107, No. 10 pp. 803–806.

Chemiluminescence: A New Method for Detecting Fluorescent Compounds Separated by Thin-Layer Chromatography, Journal of Chromatography, 134 (1977) 343–350.

Analytical Applications of Peroxyoxalate Chemiluminescence—Analytica Chimica Acta, 97 (1978) 21–27.

Fluoroimmunoassay: Present Status and Key Problems—Clin. Chem. 25/3, 353–361 (1979).

Maas et al. Dication Disulfides by Reaction of Thioureas and Related Compounds with Trifluoromethanesulfonic Anhydride. The Role of Triflic Anhydride as an Oxidizing Agent—J. Org. Chem. 1981, 46, 1606–1610.

The Anodic Bahaviour of Gold—Part I Oxidation in Acidic Solutions—Michael J. Nicol *Gold Bull.* 13, 46–55, 1980.

The Affinity of Carbon for Gold Complexes: Dissolution of Finely Disseminated Gold Using a Flow Electrochemical Cell—Gallagher et al., J. Electrochem. Soc., vol. 136, No. 9, Sep. 1989—2546–51.

Blankespoor et al. Formation and Reactions of Dithiodicarbenium Salts—J. Am. Chem. Soc., vol. 103, No. 24, 1981, pp. 7097–7101.

Kinetics and Equilibria of the S-Nitrosation of Alkylthioureas—Collings et al., J. S. Perkin II pp. 1734–36, (1975).

Reversible Oxidation of 1,3-Dithiolan-2-thione—Doyle et al., J. C. S. Chem. Comm., 1977, pp. 643–644.

Ege et al., Analytical Chemical, 56(13), 3413–17 (1984).

Ikariyama, Biochemical and Biophysical Research Communications, 128(2) at 987–92.

Keszthelyi, Csabe et al., Analytical Chemisry, Feb. 1975, pp. 249–255, vol. 47, No. 2.

LUMINESCENT METAL CHELATE LABELS AND MEANS FOR DETECTION

This application is a continuation of application Ser. No. 666,987, filed Oct. 31, 1984 now abandoned.

BACKGROUND OF THE INVENTION

There is a continuous and expanding need for rapid, highly specific methods of detecting and quantifying chemical, biochemical, and biological substances. Of particular value are methods for measuring small quantities of pharmaceuticals, metabolites, microorganisms and other materials of diagnostic value. Examples of such materials include narcotics and poisons, drugs administered for therapeutic purposes, hormones, pathogenic microorganisms and viruses, antibodies, metabolites, enzymes and nucleic acids.

The presence of these materials can often be determined by binding methods which exploit the high degree of specificity which characterizes many biochemical and biological systems. Frequently used methods are based on, for example, antigen-antibody systems, nucleic acid hybridization techniques, and protein-ligand systems. In these methods, the existence of the complex of diagnostic value is typically indicated by the presence or absence of an observable "label" which has been attached to one or more of the complexing materials.

The specific labelling method chosen often dictates the usefulness and versatility of a particular system for detecting a material of interest. A preferred label should be inexpensive, safe, and capable of being attached efficiently to a wide variety of chemical, biochemical, and biological materials without changing the important binding characteristics of those materials. The label should give a highly characteristic signal, and should be rarely, or preferably never found in nature. The label should be stable and detectable in aqueous systems over periods of time ranging up to months. Detection of the label should be rapid, sensitive, and reproducible without the need for expensive, specialized facilities or personnel. Quantification of the label should be relatively independent of variables such as temperature and the composition of the mixture to be assayed. Most advantageous are labels which can be used in homogeneous systems, i.e. systems in which separation of the complexed and uncomplexed labelled material is not necessary. This is possible if the detectability of the label is modulated when the labelled material is incorporated into a specific complex.

A wide variety of labels have been developed, each with particular advantages and disadvantages. For example, radioactive labels are quite versatile, and can be detected at very low concentrations. However, they are expensive, hazardous, and their use requires sophisticated equipment and trained personnel. Furthermore, the sensitivity of radioactive labels is limited by the fact that the detectable event can, in its essential nature, occur only once per radioactive atom in the labelled material. Moreover, radioactive labels cannot be used in homogeneous methods.

Thus, there is wide interest in non-radioactive labels. These include molecules observable by spectrophotometric, spin resonance, and luminescence techniques, as well as enzymes which produce such molecules. Among the useful non-radioactive labelling materials are organometallic compounds. Because of the rarity of some metals in biological systems, methods which specifically assay the metal component of the organometallic compounds can be successfully exploited. For example, Cais, U.S. Pat. No. 4,205,952 discloses the use of immunochemically active materials labelled with certain organometallic compounds for use in quantitating specific antigens. Any general method of detecting the chosen metals can be used with these labels, including emission, absorption and fluorescence spectrometry, atomic absorption, and neutron activation. These methods often suffer from lack of sensitivity, can seldom be adapted to a homogenous system, and as with atomic absorption, sometimes entail destruction of the sample.

Of particular interest are labels which can be made to luminesce through photochemical, chemical, and electrochemical means. "Photoluminescence" is the process whereby a material is induced to luminesce when it absorbs electromagnetic radiation. Fluorescence and phosphorescence are types of photoluminescence. "Chemiluminescent" processes entail the creation of the luminescent species by a chemical transfer of energy. "Electrochemiluminescence" entails the creation of the luminescent species electrochemically.

These luminescent systems are of increasing importance. For example, Mandle, U.S. Pat. No. 4,372,745 discloses the use of chemiluminescent labels in immunochemical applications. In the disclosed systems, the labels are excited into a luminescent state by chemical means such as by reaction of the label with $H_2O_2$ and an oxalate. In these systems, $H_2O_2$ oxidatively converts the oxalate into a high energy derivative, which then excites the label. This system will, in principle, work with any luminescent material that is stable in the oxidizing conditions of the assay and can be excited by the high energy oxalate derivative. Unfortunately, this very versatility is the source of a major limitation of the technique: typical biological fluids containing the analyte of interest also contain a large number of potentially luminescent substances that can cause high background levels of luminescence.

The present invention is concerned with electrochemiluminescent labels. Suitable labels comprise electrochemiluminescent compounds, including organic compounds and organometallic compounds. Electrochemiluminescent methods of determining the presence of labelled materials are preferred over other methods for many reasons. They are highly diagnostic of the presence of a particular label, sensitive, nonhazardous, inexpensive and can be used in a wide variety of applications. Organic compounds which are suitable electrochemical labels include, for example, rubrene and 9,10-diphenyl anthracene. Many organometallic compounds are suitable electrochemical labels, but of particular use are Ru-containing and Os-containing compounds.

The present invention is concerned with the use of Ru-containing and Os-containing labels which can be detected by a wide variety of methods. These labels are advantageous for many reasons that will be discussed herein.

Ru-containing and Os-containing organometallic compounds have been discussed in the literature. Cais discloses that any metal element or combination of metal elements, including noble metals from group VIII such as Ru, would be suitable components of organometallic labels detectable by atomic absorption methods. (Cais, column 11, line 20). However, ruthenium is not a preferred metal in Cais, osmium is not specifically mentioned, no data is presented on the efficiency of using Ru or Os in any of the methods disclosed, and the preferred method of detection, atomic absorption, entails destruction of the sample.

Weber, U.S. Pat. No. 4,293,310, discloses the use of Ru-containing and Os-containing complexes as electrochemical labels for analytes in immunoassays. The disclosed complexes are linked to amino groups on the analytes through a thiourea linkage. Weber also suggests the possibility of forming carboxylate esters between the labels and hydroxy groups on other analytes.

According to Weber, the presence of the labelled materials can be determined with an apparatus and method which comprises a quencher and an electrochemical flow cell with light means The photoelectrochemically active label upon photoexcitation transfers an electron to a quencher molecule; the oxidized molecule is subsequently reduced with an electron from an electrode of the flow cell which is held at suitable potential. This electron is measured as photocurrent. The amount of free labelled analyte in the system is determined by the photocurrent signal. Note that this method is the reverse of electrochemiluminescent detection of luminescent materials In subsequent reports, Weber et al. (1983), *Clinical Chemistry* 29, pp. 1665-1672, Photoelectroanalytical Chemistry: Possible Interferences in Serum and Selective Detection of Tris(2,2'-bipyridine)ruthenium(II) in the Presence of Interferents, have discussed the problems associated with the use of this method to detect Ru-containing labels In Table 2 of Weber et al., the extrapolated detection limit for tris(bipyridyl)ruthenium(II) is $1.1 \times 10^{-10}$ moles/L under optimal conditions. In anticipating that the actual use of these labels would entail measurements in the presence of complex mixtures, Weber et al. tested for potential interferents in their system. Table 3 of Weber et al. lists dimethylalkyl amines, EDTA, N-methylmorpholine, N,N'-dimethylpiperazine, hydroxide, oxalate, ascorbate, uric acid, and serum as interferents which would presumably raise the practical detection limit substantially above $1.1 \times 10^{-10}$ moles/L.

These studies were performed with a simple Ru-containing compound. No studies were reported in Weber or Weber et al. regarding the limits of detection of complex substances labelled with Ru-containing labels, or on whether the thiourea linkage between the labelled material and label is stable under conditions of the assay.

The particular labels with which the present invention is concerned are electrochemiluminescent. They can often be excited to a luminescent state without their oxidation or reduction by exposing the compounds to electromagnetic radiation or to a chemical energy source such as that created by typical oxalate-$H_2O_2$ systems. In addition, luminescence of these compounds can be induced by electrochemical methods which do entail their- oxidation and reduction.

Extensive work has been reported on methods for detecting $Ru(2,2'\text{-bipyridine})_3^{2+}$ using photoluminescent, chemiluminescent, and electrochemiluminescent means: Rubinstein and Bard (1981), "Electrogenerated Chemiluminescence. 37. Aqueous Ecl Systems based on $Ru(2,2'\text{bipyridine})_3^{2+}$ and Oxalate or Organic Acids", *J. Am. Chem. Soc.*, 103, pp. 512-516; and White and Bard (1982), "Electrogenerated Chemiluminescence. 41. Electrogenerated Chemiluminescence and Chemiluminescence of the $Ru(2,2'\text{-bpy})_3^{2+}$- $S_2O_8^{2-}$ System in Acetonitrile-Water Solutions", *J. Am. Chem. Soc.*, 104, p. 6891. This work demonstrates that bright orange chemiluminescence can be based on the aqueous reaction of chemically generated or electrogenerated $Ru(bpy)_3^{3+}$ (where "bpy" represents a bipyridyl ligand) with strong reductants produced as intermediates in the oxidation of oxalate ions or other organic acids. Luminescence also can be achieved in organic solvent-$H_2O$ solutions by the reaction of electrogenerated, or chemically generated, $Ru(bpy)_3^{2+}$ with strong oxidants generated during reduction of peroxydisulfate. A third mechanism for production of electrochemiluminescence from $Ru(bpy)_3^{3+}$. involves the oscillation of an electrode potential between a potential sufficiently negative to produce $Ru(bpy)_3^{3+}$ and sufficiently positive to produce $Ru(bpy)_3 3+$. These three methods are called, respectively, "oxidative-reduction," "reductive-oxidation," and "the $Ru(bpy)_3 3+/+$ regenerative system.

The oxidative-reduction method can be performed in water, and produces an intense, efficient, stable luminescence, which is relatively insensitive to the presence of oxygen or impurities. This luminescence from $Ru(bpy)_3^{2+}$ depends upon the presence of oxalate or other organic acids such as pyruvate, lactate, malonate, tartrate and citrate, and means of oxidatively producing $Ru(bpy)_3^{3+}$ species. This oxidation can be performed chemically by such strong oxidants as $PbO_2$ or a Ce(IV) salt. It can be performed electrochemically by a sufficiently positive potential applied either continuously or intermittently. Suitable electrodes for the electrochemical oxidation of $Ru(bpy)_3 2+$ are, for example, Pt, pyrolytic graphite, and glassy carbon. Although the oxalate or other organic acid is consumed during chemiluminescence, a strong, constant chemiluminescence for many hours can be achieved by the presence of an excess of the consumed material, or by a continuous supply of the consumed material to the reaction chamber.

The reductive-oxidation method can be performed in partially aqueous solutions containing an organic cosolvent such as, for example, acetonitrile. This luminescence depends upon the presence of peroxydisulfate and a means of reductively producing $Ru(bpy)_3^{1+}$ species. The reduction can be performed chemically by strong reductants such as, for example, magnesium or other metals. It can be performed electrochemically by a sufficiently negative potential applied either continuously or intermittently. A suitable electrode for the electrochemical reduction of $Ru(bpy)_3^{2+}$ is, for example, a polished glassy-carbon electrode. As with the oxidative-reduction method, continuous, intense luminescence can be achieved for many hours by inclusion of excess reagents, or by continuous addition of the consumed reagents to the reaction mixture.

The $Ru(bpy)_3^{3+}/+$ regenerative system can be performed in organic solvents such as acetonitrile or in partially aqueous systems, by pulsing an electrode potential between a potential sufficiently negative to reduce $Ru(bpy)_3^{2+}$ and a potential sufficiently positive to oxidize $Ru(bpy)_3^{2+}$. A suitable electrode for such a regenerative system is, for example, a Pt electrode. This system does not consume chemical reagents and can proceed, in principle, for an unlimited duration.

These three methods of producing luminescent Ru-containing compounds have in common the repetitive oxidation-reduction or reduction-oxidation of the Ru-containing compound. The luminescence of solutions containing these compounds is therefore highly dependent on the electric potential of the applied energy source, and is therefore highly diagnostic of the presence of a Ru-containing compound.

Mandle cites Curtis et al. (1977), "Chemiluminescence; A New Method for Detecting Fluorescent Compounds Separated By Thin Layer Chromatography", *J. Chromatography* 134, pp. 343-350, as identifying Ru-tris(bipyridyl)(II) as a possible label in chemiluminescent applications. Curtis et al. reports only unpublished observations that Ru complexes can be induced to emit light when chemically excited by an oxalate/$H_2O_2$ system (Curtis et al. p. 350).

Neither Mandle nor Curtis recognized the exceptional utility of ruthenium and osmium complexes in chemiluminescent applications or the utility of electrochemilumiscent systems. Sprintschnik, G. et al. (1977), "Preparation and Photochemical Reactivity of Surfactant Ruthenium (II) Complexes in Monolayer Assemblies and at Water-Solid Interfaces", *J. Am. Chem. Soc.* 99, pp. 4947-4954, have described complexes of tris(2,2'-bipyridine)ruthenium(II) esterified with octadecanol or dehydrocholesterol, and have created monolayer films of these surfactant complexes. The complexes were photoluminescent. But when the films were exposed to water, and then to light, the Ru-complexes failed to photoluminesce. This was attributed to photohydrolysis of ester groups in the presence of light.

It has been discovered and is disclosed herein, that a wide variety of analytes of interest and chemical moieties that bind to analytes of interest may be conveniently attached to Ru-containing or Os-containing labels through amide linkages. The labelled materials may then be determined by any of a wide variety of means, but by far the most efficient, reliable, and sensitive means are photoluminescent, chemiluminescent, and electrochemiluminescent means. It is also disclosed herein that electrochemiluminescent labels, including Ru-containing and Os-containing labels and organic molecules such as rubrene and 9,10-diphenyl anthracene, are particularly versatile and advantageous. The great advantages of the use of these novel labelled materials, and of the methods of detecting them, are further discussed hereinbelow.

SUMMARY OF THE INVENTION

According to the present invention, there is provided a chemical moiety having the formula

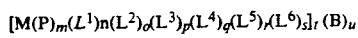

wherein M is ruthenium or osmium; P is a polydentate ligand of M; $L^1$, $L^2$, $L^3$, $L^4$, $L^5$ and $L^6$ are ligands of M, each of which may be the same as, or different from, each other ligand; B is a substance covalently bound to one or more of P, $L^1$, $L^2$, $L^3$, $L^4$, $L^5$ or $L^6$ through one or more amide linkages; m is an integer equal to or greater than 1; each of n, o, p, q, r and s is zero or an integer; t is an integer equal to or greater than 1; u is an integer equal to or greater than 1; and P, $L^1$, $L^2$, $L^3$, $L^4$, $L^5$, $L^6$ and B are of such composition and number that the chemical moiety can be induced to emit electromagnetic radiation and the total number of bonds to M provided by the ligands of M equals the coordination number of M.

The present invention provides compounds particularly suitable as intermediates for attaching a luminescent ruthenium- or osmium-containing label to amino groups of chemical, biochemical and biological substances. These intermediates are thus particularly suitable for creating chemical moieties according to the present invention. The intermediates are the mono- and di-N-hydroxysuccinimide esters of ruthenium or osmium bis(2,2'-bipyridine) (2,2'-bipyridine-4,4'-dicarboxylic acid) and their salts. These compounds may be synthesized by means known in the art.

The present invention provides methods for determining the presence of the novel chemical moieties.

The present invention also provides methods of determining the presence of a chemical moiety having the formula

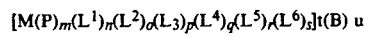

wherein M is ruthenium or osmium; P is a polydentate ligand of M; $L^1$, $L^2$, $L^3$, $L^4$, $L^5$ and $L^6$ are ligands of M, each of which may be the same, or different from, each other ligand; B is a substance which is a ligand of M or is attached to one or more of P, $L^1$, $L^2$, $L^3$, $L^4$, $L^5$ or $L^6$; m is an integer equal to or greater than 1; each of n, o, p, q, r and s is zero or an integer; t is an integer equal to or greater than 1; and u is an integer equal to or greater than 1; and P, $L^1$, $L^2$, $L^3$, $L^4$, $L^5$, $L^6$ and B are of such composition and number that the chemical moiety can be induced to emit electromagnetic radiation and the total number of bonds to M provided by the ligands of M equals the coordination number of M.

The method comprises:
a) forming a reagent mixture under suitable conditions containing the chemical moiety;
b) inducing the moiety to emit electromagnetic radiation by exposing the reagent mixture to chemical energy or electrochemical energy; and
c) detecting the emitted electromagnetic radiation and thereby determining the presence of the chemical moiety.

This invention further provides for the use of ruthenium-containing and osmium-containing labels in binding methods for determining the presence of substances of interest. These methods may be used to determine labelled moieties of interest, to employ labelled moieties to determine analytes of interest, or to use labelled analogues of analytes of interest to determine analytes of interest in competitive binding assays These binding methods may be homogeneous or heterogeneous binding methods.

Still further, the present invention provides systems for determining the presence of the ruthenium-containing or osmium-containing chemical moieties of this invention. These systems comprise a means for inducing the chemical moiety to emit electromagnetic radiation and a means for detecting the emitted electomagnetic radiation.

The present invention also provides systems for employing the ruthenium-containing or osmium-containing chemical moieties in binding methods for the determination of analytes of interest.

According to the present invention, there is provided a method of determining the presence of a chemical moiety having the formula

wherein A is a compound which can be induced to emit electromagnetic radiation by exposure to an electrochemical energy source; B is a substance which is attached to A;

k is an integer equal to or greater than 1; and u is an integer equal to or greater than 1, comprising: a) forming a reagent mixture under suitable conditions containing the chemical moiety; b) inducing the chemical moiety to emit electromagnetic radiation by exposing the reagent mixture to electrochemical energy and c) detecting the emitted electromagnetic radiation and thereby determining the presence of the chemical moiety.

The present invention also provides for use of electrochemiluminescent labels in binding methods for determining the presence of substances of interest. These methods can be used to determine labelled moieties of interest, to employ labelled moieties to determine analytes of interest, or to use labelled analogues of analytes of interest to determine analytes of interest in competitive binding assays. These binding methods can be homogeneous or heterogeneous binding methods.

A specific embodiment of the invention provides for compositions which contain two or more different chemical moieties. Each of the moieties may be chemical species which can be induced to emit electromagnetic radiation of a different wavelength. In another embodiment of the invention the chemical moieties may be chemical species each of which is induced to emit electromagnetic radiation by exposure to energy of a different value or from a different source. A different substance or analyte of interest may then be specifically attached to each of the different chemical moieties. By using these compositions and methods it is possible to determine two or more different substances or analytes of interest that may be present in the sample under examination.

DETAILED DESCRIPTION OF THE INVENTION

According to the present invention, there is provided a chemical moiety having the formula

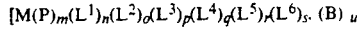

wherein M is ruthenium or osmium; P is a polydentate ligand of M; $L^1$, $L^2$, $L^3$, $L^4$, $L^5$ and $L^6$ are ligands of M, each of which may be the same as, or different from, each other ligand; B is a substance covalently bound to one or more of P, $L^1$, $L^2$, $L^3$, $L^4$, $L^5$ or $L^6$ through one or more amide linkages; m is an integer equal to or greater than 1; each of n, o, p, q, r and s is zero or an integer; t is an integer equal to or greater than 1; u is an integer equal to or greater than 1; and P, $L^1$, $L^2$, $L^3$, $L^4$, $L^5$, $L^6$ and B are of such composition and number that the chemical moiety can be induced to emit electromagnetic radiation and the total number of bonds to M provided by the ligands of M equals the coordination number of M.

This chemical moiety must have at least one polydentate ligand of M. If the moiety has greater than one polydentate ligand, the polydentate ligands may be the same or different. Polydentate ligands include aromatic and aliphatic ligands. Suitable aromatic polydentate ligands include aromatic heterocyclic ligands. Preferred aromatic heterocyclic ligands are nitrogen-containing, such as, for example, bipyridyl, bipyrazyl, terpyridyl, and phenanthrolyl.

Suitable polydentate ligands may be unsubstituted, or substituted by any of a large number of substituents known to the art. Suitable substituents include for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxysuccinimide.

This chemical moiety may have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stibines, and arsines.

Particularly preferred embodiments of this chemical moiety comprise bis(2,2'-bipyridyl)ruthenium(II) and tris(2,2'-bipyridyl)ruthenium(II).

It is within the scope of this invention for one or more of the ligands of M to be attached to additional chemical labels, such as, for example, radioactive isotopes, fluorescent components, or additional luminescent ruthenium- or osmium-containing centers.

It is also within the scope of this invention for the labelled substance (B) to be labelled by greater than one, or many, electrochemilumescent centers.

Suitable substances (B) include many biological substances, for example, whole cells, viruses, subcellular particles, proteins, lipoproteins, glycoproteins, polypeptides, nucleic acids, polysaccharides, lipopolysaccharides, cellular metabolites, hormones, pharmacological agents, tranquilizers, barbituates, alkaloids, steroids, vitamins, amino acids and sugars. Whole cells may be animal, plant, or bacterial, and, may be viable or dead. Examples include plant pathogens such as fungi and nematodes. The term "subcellular particles" is meant to encompass, for example, subcellular organelles, membrane particles as from disrupted cells, fragments of cell walls, ribosomes, multienzyme complexes, and other particles which can be derived from living organisms. Nucleic acids include, for example, chromosomal DNA, plasmid DNA, viral DNA, and recombinant DNA derived from multiple sources. Nucleic acids also include RNA's, for example messenger RNA's, ribosomal RNA's and transfer RNA's. Polypeptides include, for example, enzymes, transport proteins, receptor proteins, and structural proteins such as viral coat proteins. Preferred polypeptides are enzymes and antibodies. Particularly preferred polypeptides are monoclonal antibodies. Hormones include for example, insulin and T4 thyroid hormone. Pharmacological agents include, for example, cardiac glycosides. It is of course within the scope of this invention to include synthetic substances which chemically resemble biological materials, such as synthetic polypeptides, synthetic nucleic acids, and synthetic membranes, vesicles and liposomes. The foregoing is not intended to be a comprehensive list of the biological substances suitable for use in this invention, but is meant only to illustrate the wide scope of the invention.

It is within the scope of this invention to include labelled nonbiological substances, including polymeric materials. These substances may be in the form of soluble polymeric molecules, or any of the large variety of known macroscopic forms such as, for example, beads, or containers such as test tubes, bottles, assay wells or the like.

Biological and nonbiological substances (B) are covalently bound to a ligand of M through an amide linkage. The amide linkage may be oriented so that the material (B) is bonded directly either to the carbonyl or to the nitrogen of the amide linkage. These chemical moieties may be ionized. If so, it is understood in the art that many different counterions will serve to neutralize the charge of preparations of the chemical moiety. Suitable cations include, for example, H+, NH4+, guanidinium, Ag+, Li+, Na+, K+, Mg2+, Mn2+, and Cd2+. Suitable anions include, for example, halides, OH-, carbonate, SO4 2-, hexafluorophosphate and tetrafluoroborate.

The present invention also provides compounds particularly suitable as intermediates for attaching a luminescent ruthenium-containing or osmium-containing label to amino groups of chemical, biochemical and biological substances. These intermediates are thus particularly suitable for synthesizing chemical moieties according to the present invention. The inventive intermediates are the mono- and di-N-hydroxysuccinimide esters of ruthenium or osmium bis(2,2'-bipyridine)(2,2'-bipyridine-4,4'-dicarboxylic acid) and their salts.

The chemical structures of these intermediates are as follows. The mono-N-hydroxysuccinimide ester of ruthenium or osmium bis(2,2'-bipyridine)(2,2'-bipyridine-4,4'-dicarboxylic acid) includes

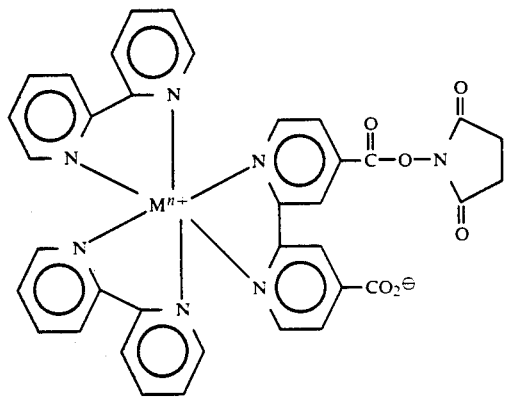

wherein M is Ru or Os, n is the integer 1, 2 or 3 and salts and stereoisomers thereof. The di-N-hydroxysuccinimide esters of ruthenium- or osmiumbis (2,2'-bipyridine)(2,2'-bipyridine-4,4' dicarboxylic acid) includes

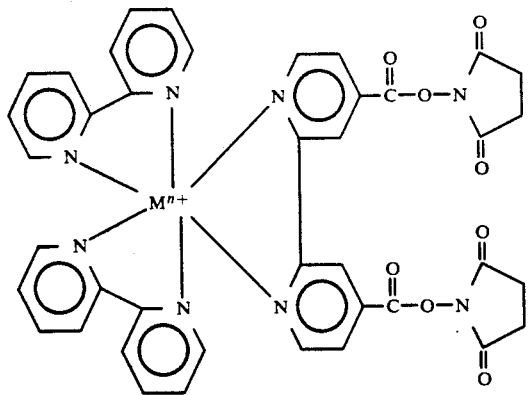

wherein M is Ru or Os, n is the integer 1, 2, or 3 and salts and stereoisomers thereof.

These compounds may be synthesized by means known to the art. A preferred method of synthesizing the ruthenium-containing compounds is to first react ruthenium dichlorobis(2,2'bipyridine) with 2,2'-bipyridine-4, 4'-dicarboxylic acid in a hot aqueous methanol solution of sodium bicarbonate. After acidification, an aqueous solution of NaPF6 is added to the solution of carboxylated ruthenium compound. The isolated hexafluorophosphate salt of the ruthenium complex is then esterified by reaction with N-hydroxy-succinimide in the presence of dicyclohexylcarbodiimide in dimethylformamide. Of course, many variations on the structure of the N-hydroxysuccinimide component are possible without substantially altering the usefulness of the inventive intermediates. These intermediates may be ionized. If so, it is understood in the art that many different counterions will serve to neutralize the charge of preparations of the intermediate. Suitable cations include for example H+, NH4+, guanidinium, Ag+, Li+, Na+, K+, Mg2+, Mn2+, and Cd2+. Suitable anions include, for example, halides, carbonate, SO4 2-, hexafluorophosphate, and tetrafluoroborate.

These intermediates are useful for labelling substances containing a free amino group capable of attacking the carboxylate ester, and thereby displacing N-hydroxysuccinimide. Use of these intermediates to label analytes of interest is preferred over the isothiocyanates of the prior art (e.g. Weber, U.S. Pat. No. 4,293,310). Isothiocyanates are generally prepared by reaction of a primary amine with carbon disulfide or thiophosgene, each of which is volatile and highly. Carbon disulfide is also an acute fire and explosion hazard. The required precursor primary aromatic amines are more difficult to obtain than the precursor aromatic carboxylic acids used in the present invention. Also, the active ester intermediates of the present invention are less reactive and more easily stored and handled than the isothiocyanate derivatives.

The present invention provides methods for determining the presence of chemical moieties according to this invention. The metal-containing compositions may be detected by many means known to the art including, for example, emission, absorption, and fluorescence spectrometry, atomic absorption, anodic stripping voltametry, neutron activation and electrochemical methods. Of particular interest are photoluminescence, chemiluminescence and electrochemiluminescence methods.

Ru(bpy)3 2+ may be determined at very low concentrations using luminescence techniques. Using the oxidative reduction method, Ege et al. (1984) (Analytical Chemistry, in press) were able to detect Ru(bpy)3 2+ at concentrations of $5\times10^{-8}$ M. In these experiments, sodium oxalate was 1 mM in phosphate buffer pH 5.0, and the potential was pulsed at +1.0 to +1.4 volts versus a saturated sodium chloride reference electrode for 5 to 10 second intervals. These workers found the reductive oxidation method to be even more sensitive. Using 18 mM Na2S2O8 and 0.1M tetra-n-butyl ammonium tetrafluoroborate in CH3CN: H2O (1:1 v/v), Ru(bpy)3 2+ concentrations as low as $10^{-13}$ M could be detected. Further refinements of the techniques promise even greater sensitivity. These techniques also provide sensitive and accurate measurements of labelled substances, as demonstrated more fully in the Examples set out hereinbelow.

Our experience with Ru(bpy)3 2+-labelled substances indicates the advantages of using ruthenium-containing and osmium-containing compounds as chemical labels. They are stable for long periods and may be attached efficiently to a wide variety of chemical, biochemical and biological materials. The labels are safe and relatively inexpensive. They give a highly characteristic signal and do not occur in nature. Measurements based on luminescence of the labels are sensitive, fast, reproducible and utilize simple instrumentation. There is very little interference with detection based on luminescence of these labels by such components as phosphate buffered saline, Tween ® (a surfactant), liver tissue extract or serum. Luminescence-based measurement of these labels does not destroy the sample or labelled materials and may be performed repetitively. The signal is generated repeatedly by each molecule of label, thereby enhancing the sensitivity with which these labels may be detected. The presence of labelled materials may be determined qualitatively or quantitatively depending on the needs of the particular application. Note: the word "determined", as used in this patent application, refers to either qualitative or quantitative determinations of the labelled material.

Accordingly, this invention provides a method of determining the presence of a chemical moiety having the formula

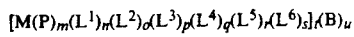

$[M(P)_m(L^1)_n(L^2)_o(L^3)_p(L^4)_q(L^5)_r(L^6)_s](B)_u$ wherein M is ruthenium or osmium; P is a polydentate ligand of M; $L^1$, $L^2$, $L^3$, $L^4$, $L^5$ and $L^6$ are ligands of M, each of which may be the same as, or different from each other ligand; B is a substance which is a ligand of M or is attached to one or more of P, $L^1$, $L^2$, $L^3$, $L^4$, $L^5$ or $L^6$; m is an integer equal to or greater than 1; each of n, o, p, q, r and s is zero or an integer; t is an integer equal to or greater than 1; u is an integer equal to or greater than 1 and P, $L^1$, $L^2$, $L^3$, $L^4$, $L^5$, $L^6$ and B are of such composition and number that the chemical moiety can be induced to emit electromagnetic radiation and the total number of bonds to M provided by the ligands of M equals the coordination number of M.

The method comprises:
a) forming a reagent mixture under suitable conditions containing the chemical moiety;
b) inducing the moiety to emit electromagnetic radiation by exposing the reagent mixture to chemical energy or electrochemical energy; and
c) detecting the emitted electromagnetic radiation and thereby determining the presence of the analyte of interest.

In the chemical moieties useful in these methods, biological and nonbiological substances (B) may be incorporated into the moieties by coordination directly to M or by attachment to a ligand of M. Attachment may be through covalent bonding, or by electrostatic or hydrogen bonding. Many diverse means of effecting covalent bonding of substances (B) to ligands of M are available. The attaching linkage may be, for example, an amide bond, an ester or thioester linkage, an ether or thioether linkage or any of many other means known to the art. The type of linkage will be determined by the suitable chemical substituents of the ligand and the suitable chemical groups available for binding with the ligand on the substance that is to be labelled. Suitable substances (B) include for example, whose cells, subcellular particles, nucleic acids, polysaccharides, proteins, glycolipoproteins, lipopolysaccharides, polypeptides, cellular metabolites, hormones, pharmacological agents, tranquilizers, barbituates, alkaloids, steroids, vitamins, amino acids, sugars, and non-biological polymers. In a preferred embodiment of the invention the attaching linkage is an amide bond. The amide bond is formed between the substituent on the ligand and a free amino group on the substance that is to be labelled.

These methods include a method of determining the chemical moiety by formation of a specific complex with a complementary material. Of particular interest are antibody-antigen pairs of materials. This binding method may be used to determine the presence of labelled antigens, such as, for example, digoxin or digitoxin in complex mixtures such as blood, urine, or synthetic reaction mixtures by first exposing the mixture to immobilized antibodies specific for the antigen of interest, and then measuring the amount of labelled material bound to the immobilized antibodies.

The phrase "inducing to emit electromagnetic radiation" refers to creating an excited state of said moiety which luminesces at wavelengths between 200 nanometers and 900 nanometers at ambient temperatures. The present invention envisions osmium-containing moieties as well as ruthenium-containing moieties and encompasses the wide variety of luminescent moieties which can be made by varying the chemical structure of the ligands. Each of these variations in the metal and the ligands can change the precise value of the energy input required to create the luminescent excited state. Similarly, the wavelength of the emitted electromagnetic radiation will be dependent upon the nature and environment of the ruthenium-containing or osmium-containing material. Generally, photoluminescence excitation and emission will occur with electromagnetic radiation of between about 200 nanometers and about 900 nanometers in wavelength. Chemiluminescent and electrochemiluminescent emission will generally occur with the emitted electromagnetic radiation being between about 200 nanometers and about 900 nanometers in wavelength. The potential at which the reduction or oxidation of the chemical moiety will occur depends upon its exact chemical structure as well as factors such as the pH of the solution and the nature of the electrode used. Generally, it is well known in the art how to determine the optimal emission and excitation wavelengths in a photoluminescent system, and the optimal potential and emission wavelength of an electrochemiluminescent or chemiluminescent system.

It should be clear that there are many methods for quantifying the amount of luminescent species present. The rate of energy input into the system can provide a measure of the luminescent species. Suitable measurements include, for example, measurements of electric current when the luminescent species is generated electrochemically, the rate of reductant or oxidant utilization when the luminescent species is generated chemically or the absorption of electromagnetic energy in photoluminescent techniques. In addition, of course, the luminescent species can be detected by measuring the emitted electromagnetic radiation. All of these measurements can be made either as continuous, rate-based measurements, or as cumulative methods which accumulate the signal over a long period of time. An example of rate-based measurements is the use of photomultiplier tubes, photodiodes or phototransistors to produce electric currents proportional in magnitude to the incident light intensity. Examples of cumulative methods are the integration of rate-based data, and the use of photographic film to provide cumulative data directly.

All of these luminescence-based methods entail repeated luminescence by the ruthenium-containing compound. The repetitive nature of the detectable event distinguishes these labels from radioactive isotopes or bound chemiluminescent molecules such as luminol. The latter labels produce a detectable event only once per molecule (or atom) of label, thereby limiting their detectability.

This invention further provides for the use of ruthenium-containing and osmium-containing labels in binding methods for determining the presence of analytes of interest. Many such binding methods are known to the art. These methods often exploit the great specificity with which biochemical and biological agents bind together. Examples are methods based on nucleic acid hybridization techniques, antibody-antigen based techniques, and enzyme-ligand based techniques. These methods can employ labelled moieties to determine analytes of interest or to use labelled analogues of analytes of interest to determine analytes of interest in competitive binding assays.

The analyte of interest and the chemical moiety can be any pair of substances which are capable of binding together in a specific manner. Such substances include for example, whole cells, subcellular particles, nucleic acids, polysaccharides, proteins, glycoproteins, lipoproteins, lipopolysaccharides, polypeptides, cellular metabolites, hormones, pharmacological agents, tranquilizers, barbituates, alkaloids, steroids, vitamins, amino acids, sugars, and non-biological polymers. Of particular interest are antibody-antigen pairs. For example, this method encompasses the use of labelled antibodies to determine the presence of cell surface antigens, or to label particular cells for detection by cell sorting methods. Antigens immobilized by, for example, attachment to immobilized, unlabelled antibodies can be detected by labelled antibodies in a method commonly known as a "sandwich" method.

In competitive binding assays, the analyte of interest and the labelled analogue of the analyte can be any substances capable of participating in formation of a specific complex with a complementary material, such as for example, whole cells, subcellular particles, nucleic acids, polysaccharides, proteins, glycoproteins, lipoproteins, lipopolysaccharides, polypeptides, cellular metabolites, hormones, pharmacological agents, tranquilizers, barbituates, alkaloids, steroids, vitamins, amino acids, sugars and non-biological polymers. Of particular interest are antibody-antigen-based methods. These methods are analogous to the well known radioimmunoassay, wherein an analyte of interest is detected when it displaces a radioactive analogue of the analyte from an antibody. The many variations on radioimmunoassay known to the art can, in principle, be used to advantage by employing moieties labelled according to the present invention in place of radioactively labelled compounds.

It is further provided by the present invention to use labelled chemical moieties in either heterogeneous or homogeneous binding methods. In heterogeneous binding methods, the bound labelled substance must be physically separated from the unbound labelled substance before measurement of the presence of label. This is frequently accomplished in antibody-antigen systems by immobilizing one component, the antibody for example, by attachment to an insoluble matrix such as a filter or to the surface of beads or reaction vessels such as test tubes. The antigen-containing solution is poured through the filter or into the reaction vessel, and then washed away from the filter or sides of the reaction vessel. Only antigen specifically bound to antibody will remain to be determined.

In homogeneous methods, by contrast, the bound and unbound labelled material are present in the same reaction mixture when the presence of label is measured. This is possible when binding modifies the properties of the signal detectable from the label. There are many ways that luminescent labels can be used in homogeneous systems. For example, if a luminescence quencher were properly positioned on an antibody, binding of a labelled antigen could result in suppression of the luminescence of the label by the luminescence quencher on the antibody. Many homogeneous methods for luminescent labels are known to the art, and some of them are reviewed in Boguslaski and Li (1982), "Homogeneous Immunoassays," *Applied Biochemistry and Biotechnology*, 7, pp. 401–414.

A particularly unique and useful class of homogeneous binding assays is provided by the present invention. As described hereinbefore, these labels can be measured electrochemically by means of exposing a solution of the labelled substance of interest to an electrode. Any labelled substance which is present in the solution but cannot gain access to the surface of the electrode will not be detected. This can occur, for example, if the labelled substance is bound directly or indirectly to the surface of the reaction vessel into which the electrode is placed, or if the label is imbedded deep into the interior of the specific complex, such as within an antigen-antibody complex, or if the electrode itself were coated with a layer through which labelled material could pass but complexed labelled material could not pass. In addition, it should be possible to coat the surface of an electrode with antibodies, so that only labelled antigen bound to the immobilized antibodies can obtain access to the electrode and thereby be determined. This particular homogenous method may be most effective if the required electrode potential is applied in short pulses.

It is within the scope of the present invention to use a combination of means for determining the presence of labelled compounds. For example, it may be desirable to measure the total amount of labelled substance by a means which does not distinguish between bound and unbound labelled substance such as photoluminescence or chemiluminescence, and to determine the amount of bound labelled substance by a means which does distinguish between bound and unbound labelled substance, such as electrochemiluminescence, for example. Such a combination of methods could be performed on the same sample, and thus provide a richer source of information about the sample than could any method when used individually. It is also within the scope of this invention to determine the presence of two or more differently labelled compounds within the same reaction mixture This is possible either if the labels emit electromagnetic radiation of differing wavelengths or if the labels can be induced to emit electromagnetic radiation by exposure to energy of different values or sources.

The present invention further provides systems for determining the presence of the ruthenium-containing or osmium-containing chemical moieties The systems comprise reagent mixtures comprising the chemical moiety, a means for inducing the chemical moiety to emit electromagnetic radiation, and a means for detecting the emitted electromagnetic radiation.

The present invention further provides systems for employing ruthenium-containing or osmium-containing labelled chemical moieties for the determination of analytes of interest.

The systems of the present invention are envisioned to be useful in the rapid, efficient, and versatile performance of the diverse methods disclosed and suggested by the instant invention disclosure.

This invention also provides a method of determining the presence of a chemical moiety having the formula $(A)_k(B)_u$. A is a compound which can be induced to emit electromagnetic radiation by exposure to an electrochemical energy source. These compounds can be inorganic, organometallic or organic compounds, e.g. rubrene, 9,10-diphenyl anthracene, or ruthenium-containing or osmium-containing labels. B is a substance which is attached to A, k is an integer equal to or greater than one and n is an integer equal to or greater than 1.

The method comprises forming a reagent mixture under suitable conditions containing the chemical moiety and inducing the chemical moiety to emit electromagnetic radiation by exposing the reagent mixture to electrochemical energy. The emitted electromagnetic radiation is then detected by suitable methods thereby determining the presence of the chemical moiety.

Biological and nonbiological substances (B) may be incorporated into the moieties by any form of attachment to A. The attachment may be by coordination to a metal atom present in A or to a ligand of A. The attachment can be through covalent, electrostatic, or hydrogen bonding. The type of linkage will be determined by the suitable chemical groups available for binding on both A and B.

Suitable substances (B) include, for example, whole cells, subcellular particles, nucleic acids, polysaccharides, proteins, glycoproteins, lipoproteins, lipopolysaccharides, polypeptides, cellular metabolites, hormones, pharmacological agents, tranquilizers, barbituates, alkaloids, steroids, vitamins, amino acids and sugars. The substances are not limited to biological substances and may be any suitable non-biological substance such as a polymer, organic or inorganic compound.

The chemical moiety is induced to emit electromagnetic radiation by creating an excited state of the moiety which luminesces at wavelengths from about 200 nanometers to about 900 nanometers at ambient temperatures. In this embodiment of the invention the chemical moiety is excited by exposing the reagent mixture to electrochemical energy. The potential at which the reduction or oxidation of the inventive chemical moiety will occur depends upon its exact chemical structure as well as factors such as the pH of the solution and the nature of the electrode used. It is well known to those of ordinary skill in the art how to determine the optimal potential and emission wavelength of an electrochemiluminescent system. The electrochemiluminescent species may be measured by any suitable measurement such as the measurement of electric current or emitted electromagnetic radiation.

The method of determining the presence of the moiety may also be performed when the moiety is capable of binding to another chemical agent. The chemical agent may be any substance capable of binding to the moiety in a specific manner. Examples of such methods are nucleic acid hyridization techniques, antibody-antigen based techniques and enzyme-ligand techniques.

In another embodiment of the invention the electrochemiluminescent moiety, $(A)_k(B)_u$ may be used in methods to determine the presence of an analyte of interest which binds to the moiety.

The analyte of interest can be any substance which is capable of binding to the electrochemiluminescent moiety, such as the binding of an antigen to a antibody labelled with an electrochemiluminescent moiety. The method involves contacting the analyte with the chemical moiety under suitable conditions so as to form a reagent mixture. The chemical moiety is then induced to emit electromagnetic radiation by exposing the reagent mixture to electrochemical energy. The presence of the analyte is determined by detecting the electromagnetic radiation emitted by the chemical moiety bound to the analyte.

Competitive binding methods may also be used to determine the presence of an analyte of interest. The analyte and the chemical moiety, $(A)_k(B)_u$, bind competitively to a chemical material. The material is contacted with the chemical moiety and analyte under suitable conditions so as to form a reagent mixture. The chemical moiety is induced to emit electromagnetic radiation by exposing the mixture to electrochemical energy. The presence of the analyte of interest is determined by detecting the amount of emitted electromagnetic radiation.

This invention also concerns compositions which comprise the ruthenium-containing or osmium-containing chemical moieties of this invention and one or more different chemical moieties each of which can be induced to emit electromagnetic radiation of a different distinct wavelength. These compositions are useful in methods and systems of detecting two or more different substances or analytes of interest contained in a mixture of the same and other substances.

The other different chemical moiety or moieties may be any suitable chemical moiety such as inorganic, organic and organometallic compounds which can be induced to emit electromagnetic radiation, e.g. rubrene or 9,10-diphenylanthracene. These moieties may be such moieties that are induced to emit electromagnetic radiation when exposed to energy of different values or sources than the energy used to induce electromagnetic radiation from the rutheniumcontaining or osmium-containing chemical moieties. In a specific embodiment of the invention, each other chemical moiety emits electromagnetic radiation of a different distinct wavelength when induced to emit electromagnetic radiation by energy of the same source and value that induces the ruthenium-containing or osmium-containing chemical moiety to emit electromagnetic radiation.

Methods for determining these chemical moieties comprise forming a reagent mixture under suitable conditions containing the chemical moieties and then inducing the chemical moieties to emit electromagnetic radiation by exposing the reagent mixture to chemical energy or electrochemical energy. The presence of each of the moieties is determined by detecting the electromagnetic radiation of different wavelengths emitted by each of the moieties.

The invention also concerns a method of determining the presence of one or more analytes of interest which bind selectively to the different chemical moieties present in the same mixture. The method comprises contacting the analytes with the chemical moieties under suitable conditions so as to form a reagent mixture. The moieties are induced to emit electromagnetic radiation by exposing the reagent mixture to chemical energy or electrochemical energy and the emitted electromagnetic radiation of different wavelengths is detected to determine the presence of each of the analytes of interest These methods in which the presence of two or more chemical moieties is determined in a mixture are applicable to all instances described previously for determining the ruthenium-containing and osmium-containing luminescent labels. This embodiment, however, allows for the determination of two or more different substances present in the same sample simultaneously.

In another embodiment of the invention the different chemical moieties are induced to emit electromagnetic radiation by exposure to energy of different values or different sources. The methods of determining these different chemical moieties are essentially the same as those for determining the chemical moieties which emit different wavelengths of electromagnetic radiation, except for the induction step. These chemical moieties are induced to emit electromagnetic radiation by energy of different values or sources. The sample containing the moieties is exposed to each of the different energy values or sources at a different time and the emitted electromagnetic radiation emitted by the specific moiety is detected, thus determining the presence of the moiety. This method is also useful for determining the presence of analytes of interest which bind selectively to the different chemical moieties present in the sample.

Another embodiment of the invention involves methods and systems of determining one or more different electrochemiluminescent moieties of the formula $(A)_k(-B)_u$ present in the same sample. These chemical moieties contain different compounds which emit electromagnetic radiation of different wavelengths when exposed to an electrochemical energy source or can each be induced to emit electromagnetic radiation by exposure to distinct electrochemical energy sources. These different electrochemiluminescent moieties may be specifically attached to different substances or analytes of interest. Determination of the different moieties involves the same procedures as discussed previously.

This invention is illustrated in the examples which follow. The examples are set forth to aid in an understanding of the invention but are not intended to, and should not be construed to, limit in any way the invention as set forth in the claims which follow thereafter.

EXAMPLE I

Preparation of Ruthenium bis (2,2'-bipyridine) (2,2'-bipyridine-4,4'-dicarboxylic acid) bis(hexafluorophosphate).

Sodium bicarbonate (0.40 g), ruthenium dichlorobis(2,2'-bipyridine)(0.40 g), and 2,2'-bipyridine-4,4'-dicarboxylic acid (0.30 g) were stirred in refluxing methanol (20 ml)-water (5 ml) for 9 hours. The resulting solution was cooled in an ice bath, treated with 5 drops concentrated $H_2SO_4$, and allowed to stand at ice temperature for 1.5 hours. A precipitate formed, which was separated by filtration and washed with MeOH (8 ml).

The combined filtrate and wash solution were treated with a solution of sodium hexafluorophosphate (5.0 g) in water (25 ml). The resulting solution was cooled in an ice bath for 3 hours, and the resulting precipitate of red-purple crystals was collected by filtration (0.40 g).

EXAMPLE II

Preparation of Active Ester of Ruthenium bis(2,2'-bipyridine) (2,2'-bipyridine-4,4'-dicarboxylic acid).

Dicyclohexylcarbodiimide (DCC, 0.046 g) and N-hydroxysuccinimide (0.034 g) were dissolved in DMF (2 ml) with stirring, and cooled in an ice bath. A solution of ruthenium bis (2,2'-bipyridine) (2,2'-bipyridine-4,4'-dicarboxylic acid) (0.101 g, prepared as in Example I) dissolved in DMF (1 ml) was added, and the mixture was stirred 5 hours at ice bath temperature. A precipitate formed and was separated by centrifugation. The supernatant containing the activated ruthenium complex was retained for labelling of substrates.

EXAMPLE III

Labelling of Bovine Serum Albumin (BSA) with Activated Ruthenium Complex.

The DMF solution of activated ruthenium complex prepared in Example II (1 ml) was added to a stirred solution of BSA in aqueous Physiologic Buffered Saline (PBS, 5 ml; 25 mg/ml BSA). The mixture was stirred overnight, and precipitate was removed by centrifugation. The supernatant containing ruthenium-labelled BSA was analyzed by two methods.

METHOD 1: Dialysis

Ruthenium-labelled BSA solution was dialyzed with PBS solution. As a control, the unbound, activated ruthenium complex prepared in Example II was also dialyzed with PBS solution. After 8 hours, the control showed no fluorescent species within the dialysis tube. The ruthenium labelled BSA solution, however, showed strong fluorescence, indicating that the ruthenium complex was bound to the high molecular weight BSA.

METHOD 2: Microfiltration

Ruthenium-labelled BSA solution was placed in an Amicon microconcentrator and centrifuged at 8000 rpm. A small fraction of red-orange solution remained above the filter, and this colored fraction was diluted with wash PBS solution and centrifuged. This procedure was repeated several times. After the fourth wash, colorless solution passed through the filter, while highly red-orange colored material remained above the filter. This result indicates that the ruthenium complex was bound to the high molecular weight BSA.

EXAMPLE IV

Labelling of Human Immunoglobulin G (IgG) with Activated Ruthenium Complex.

The DMF solution of activated ruthenium complex prepared in Example II was added to a stirred solution of affinity purified human IgG in aqueous buffer. The ruthenium labelled IgG solution fluoresced brightly after extensive dialysis, indicating that the ruthenium complex was bound to the high molecular weight affinity purified human IgG.

EXAMPLE V

Labelling of Rabbit Anti-salmonella Antibody

The DMF solution of activated ruthenium complex prepared in Example II (0.1 ml) was stirred with rabbit serum containing anti-Salmonella antibody (1 ml) at room temperature for 1 hour, and then quenched by addition of diethanolamine (0.1 ml). Salmonella cells were treated with the resultant solution containing ruthenium labelled anti-Salmonella antibody. The cells were separated by centrifugation and resuspended in fresh buffer five times, in order to separate the cells from any unbound antibody (including ruthenium labelled unbound antibody) and from any free ruthenium complex. The Salmonella cells, treated with ruthenium labelled anti-Salmonella antibody, emitted bright red-orange light when viewed on a fluorescence optical microscope, indicating that the anti-Salmonella antibody was labelled with ruthenium complex, and that the ruthenium labelled antibody retained its ability to bind to Salmonella cells under conditions where the ruthenium complex fluoresced.

EXAMPLE VI

The procedure of Example V was repeated using normal mouse serum (i.e., lacking anti-Salmonella antibody) in place of rabbit serum containing anti-Salmonella antibody. The Salmonella cells, after treatment, did not emit red-orange light when viewed on a fluorescence optical microscope, indicating that non-specific binding of ruthenium labelled normal mouse serum components to Salmonella cells did not occur.

EXAMPLE VII

Labelling of Goat Anti-Rabbit Immunoglobulin (IgG) and Comparison with Rhodamine

The DMF solution of activated ruthenium complex prepared in Example II was added to a stirred solution of affinity purified goat anti-rabbit IgG. After reaction, the mixture was dialyzed against buffer. Material remaining in the dialysis tube fluroresced under UV light.

The ruthenium labelled IgG was tested for reactivity toward Salmonella coated with rabbit anti-Salmonella antibodies. Rabbit anti-Salmonella antibodies were reacted *Salmonella worthington* that had been fixed to a glass microscope slide, and unreacted antibody was washed away with buffer. The ruthenium labelled goat anti-rabbit IgG was then reacted with the antibody treated *S. worthington*, and unreacted material was washed away with buffer. The slide was examined under an optical microscope equipped with a 50 W mercury lamp, and very bright orange-red fluorescence was observed on and around the bacterium.

A control experiment tested for non-specific binding of ruthenium-labelled antibody. *S. worthington*, fixed to a glass microscope slide, was reacted with normal mouse serum, and then with ruthenium labelled goat anti-rabbit IgG antiserum. The same washing procedures were followed. No orange-red fluorescence was observed.

For comparison purposes, a thodamine isothiocyanate conjugated goat anti-rabbit IgG antiserum (at a protein concentration equivalent to the ruthenium-conjugated antibody) was reacted with *S. worthington* coated with rabbit anti-*Salmonella* antibodies. Red fluorescene was barely detectable and the intensity of fluorescence was significantly less than the ruthenium conjugate.

EXAMPLE VIII

Electrochemiluminescent (ECL) Detection of Ruthenium Labelled Bovine Serum Albumin (BSA)

ECL measurements were carried out in a one compartment cell (30 ml) with an optically flat bottom. The working electrode was glassy carbon, the counter electrode was platinum gauze, and the pseudo-reference electrode was a silver wire. Light intensity measurements were made by applying a potential of $-2.0$ v (versus the Ag wire), detecting the emitted light with a photomultiplier tube (Hamanatsu 928), and integrating the resulting signal for 2 s with a Bascom-Turner Recorder.

Acetonitrile-water (9 ml, 50:50 v/v), tetrabutylammonium tetrafluoroborate (329 mg), and diammonium peroxydisulfate (42 mg) were mixed in the ECL cell, and background light intensity was recorded. Ruthenium labelled BSA solution (prepared in Example III) was diluted in acetonitrile-water (50:50 v/v) and the diluted BSA solution (1 ml) was added to the ECL cell. The resulting solution was deaerated by bubbling solvent-saturated nitrogen. Table I summarizes results for different concentrations of ruthenium labelled BSA.

TABLE I

| Light Intensity (Arbitrary Units) | (Ruthenium) (M) |
|---|---|
| 5.2 | blank |
| 20.63 | $1 \times 10^{-11}$ |
| 33.25 | $1 \times 10^{-10}$ |
| 54.42 | $9 \times 10^{-10}$ |
| 150.2 | $8 \times 10^{-9}$ |

What is claimed is:

1. A chemical moiety having the formula

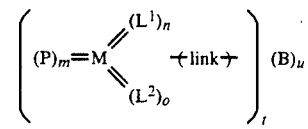

wherein:

M is ruthenium or osmium;

P, $L^1$, and $L^2$ each is a bidentate aromatic heterocyclic nitrogen-containing ligand of M selected from the group consisting of bipyridyl, substituted bipyridyl, bipyrazyl, substituted bipyrazyl, phenanthroylyl and substituted phenanthroyl, wherein each of said substituted groups is substituted by an alkyl, aryl, aralkyl, carboxylate, carboxyaldehyde, carboxamide, cyano, amino, hydroxycarbonyl, hydroxyamino, aminocarbonyl, amidine, guanidinium, ureide, sulfur-containing group, phosphorus-containing group, or the carboxylate ester of N-hydroxysuccinimide, each of said ligands being the same or not the same as each other ligand;

B is a biological substance, a synthetic substance which is capable of competing with a biological substance in a competitive binding reaction with a complementary material, or a non-biological polymer;

m is 1;

each of n and o is 1;

t is an integer equal to or greater than 1;

u is 1; and said link is one or more amide linkages, each said amide linkage covalently bonding B with one of P, $L^1$ and $L^2$;

P, $L^1$, $L^2$, and B being of such composition and number that the chemical moiety is capable of being inducted to electrochemiluminesce, and the total number of bonds to M provided by the ligands of M equals the coordination number of M.

2. A chemical moetiy as defined in claim 1, wherein said link is the linkage formed between a carboxyl group and a free amino group which is part of B.

3. A chemical moiety as defined in claim 1, wherein each bidentate ligand is said bipyridyl or said substituted bipyridyl.

4. A chemical moiety as defined in claim 1, wherein M is ruthenium.

5. A chemical moiety as defined in claim 1, wherein M is osmium.

6. A chemical moiety as defined in claim 1, wherein B is whole cell, subcellular particle, polypeptides, nucleic acid, polysaccharide, alkaloid, steroid, vitamin, amino acid, or non-biological polymer.

7. A chemical moiety as defined in claim 1, wherein B is a plant pathogen.

8. A chemical moiety as defined in claim 1, wherein B is a serum-derived antibody or a monoclonal antibody.

9. A chemical moiety as defined in claim 1, wherein B is T4 thyroid hormone.

10. A chemical moiety as defined in claim 1, wherein the amide linkage covalently bonds B with a substituted bipyridyl ligand and the amide linkage is oriented so that the carbonyl group of the amide linkage is bonded directly to said substituted bipyridyl ligand.

11. A chemical moiety as defined in claim 1 containing two bipyridyl ligands and one substituted bipyridyl ligand.

12. A chemical moiety as defined in claim 1, wherein B is a protein or a nucleic acid.

* * * * *

UNITED STATES PATENT AND TRADEMARK OFFICE
CERTIFICATE OF CORRECTION

PATENT NO. : 5,221,605
DATED : October 30, 1990
INVENTOR(S) : A.J. Bard and G.M. Whitesides It is certified that error appears in the above-identified patent and that said Letters Patent is hereby corrected as shown below:

On the title page, delete "[*] Notice: The portion of the term of this patent subsequent to Apr. 27, 2007 has been disclaimed."

Signed and Sealed this

Twenty-eighth Day of December, 1993

Attest:

BRUCE LEHMAN

Attesting Officer          Commissioner of Patents and Trademarks